(12) United States Patent
Nino et al.

(10) Patent No.: US 10,716,687 B2
(45) Date of Patent: Jul. 21, 2020

(54) FLEXIBLE ADJUSTABLE RADIOPAQUE TRIAL, PLATE AND METHOD OF USE

(71) Applicant: ECA Medical Instruments, Thousand Oaks, CA (US)

(72) Inventors: John Nino, Simi Valley, CA (US); Michael J. Milella, Jr., Thousand Oaks, CA (US); Lauren Thelen, Thousand Oaks, CA (US)

(73) Assignee: ECA Medical Instruments, Newbury Park, CA (US)

( * ) Notice: Subject to any disclaimer, the term of this patent is extended or adjusted under 35 U.S.C. 154(b) by 0 days.

(21) Appl. No.: 15/960,443

(22) Filed: Apr. 23, 2018

(65) Prior Publication Data

US 2018/0235778 A1 Aug. 23, 2018

Related U.S. Application Data

(63) Continuation-in-part of application No. 15/588,375, filed on May 5, 2017, now abandoned, which is a
(Continued)

(51) Int. Cl.
*A61F 2/44* (2006.01)
*A61F 2/46* (2006.01)
(Continued)

(52) U.S. Cl.
CPC ........ *A61F 2/4684* (2013.01); *A61B 17/1728* (2013.01); *A61B 17/7059* (2013.01);
(Continued)

(58) Field of Classification Search
CPC . A61B 17/80; A61B 17/8863; A61B 17/8052; A61B 17/8057; A61B 17/8085;
(Continued)

(56) References Cited

U.S. PATENT DOCUMENTS 4,959,065 A * 9/1990 Arnett ................ A61B 17/8085
606/285
5,438,242 A * 8/1995 Simpson ................ H05B 41/24
315/219
(Continued)

FOREIGN PATENT DOCUMENTS

WO    WO 2014/158680    10/2014

OTHER PUBLICATIONS

International Search Report and Written Opinion dated Feb. 17, 2016 in International Patent Application No. PCT/US2015/029290.
(Continued)

*Primary Examiner* — Pedro Philogene
(74) *Attorney, Agent, or Firm* — Ferguson Case Orr Paterson (57) ABSTRACT

A flexible plastic, resin or polymer material forming a trial plate for use is surgery of bones including spine and extremities. The trial plate having at least one radioopaque region and which may have one radiolucent region. In some instances a main body includes one or more arms formed of subparts. Between the main body and subparts and between the subparts are rangible regions such a ribs or unbroken edges surrounding windows configured as predetermined break points to disassociate portions of an arm from the whole.

18 Claims, 10 Drawing Sheets

Related U.S. Application Data continuation of application No. PCT/US2015/059290, filed on Nov. 5, 2015, application No. 15/960,443, which is a continuation-in-part of application No. PCT/US2017/057841, filed on Oct. 27, 2017.

(60) Provisional application No. 62/075,717, filed on Nov. 5, 2014, provisional application No. 62/413,896, filed on Oct. 27, 2016.

(51) Int. Cl.
*A61B 17/80* (2006.01)
*A61B 17/17* (2006.01)
*A61B 17/70* (2006.01)
*A61F 2/30* (2006.01)
*A61B 90/00* (2016.01)

(52) U.S. Cl.
CPC .......... *A61B 17/80* (2013.01); *A61B 17/8061* (2013.01); *A61F 2/442* (2013.01); *A61B 17/1757* (2013.01); *A61B 17/1782* (2016.11); *A61B 2090/3966* (2016.02); *A61F 2/4455* (2013.01); *A61F 2/4603* (2013.01); *A61F 2/4611* (2013.01); *A61F 2002/3008* (2013.01); *A61F 2002/30056* (2013.01); *A61F 2002/30578* (2013.01); *A61F 2002/30616* (2013.01); *A61F 2002/30672* (2013.01); *A61F 2002/4629* (2013.01)

(58) Field of Classification Search
CPC . A61B 17/8605; A61B 17/86; A61B 17/7059; A61B 17/8047; A61B 17/8061; A61B 17/8004; A61F 2/4684; A61F 2/442; A61F 2/4455; A61F 2/4611; A61F 2005/30056; A61F 2002/3008; A61F 2002/30578; A61F 2002/30616; A61F 2002/30672; A61F 2002/4623; A61F 2002/4629
USPC ....... 606/246–289, 151, 213, 215, 219, 220; 623/17.11–17.16
See application file for complete search history.

(56) References Cited

U.S. PATENT DOCUMENTS

| | | | |
|---|---|---|---|
| 6,206,882 B1 * | 3/2001 | Cohen | A61B 17/7059 606/283 |
| 6,506,191 B1 * | 1/2003 | Joos | A61B 17/8033 606/280 |
| 6,656,181 B2 | 12/2003 | Dixon et al. | |
| 7,077,844 B2 * | 7/2006 | Michelson | A61B 17/1604 606/247 |
| 7,247,169 B1 | 7/2007 | Lo et al. | |
| 8,118,847 B2 * | 2/2012 | Wallenstein | A61B 17/8033 606/286 |
| 8,133,282 B2 | 3/2012 | Hushka et al. | |
| 2005/0027300 A1 | 2/2005 | Hawkins et al. | |
| 2008/0091199 A1 | 4/2008 | Cragg | |
| 2014/0180339 A1 | 6/2014 | Ritland | |
| 2015/0313652 A1 * | 11/2015 | Burckhardt | A61B 17/80 606/71 |
| 2017/0020683 A1 | 1/2017 | Bray, Jr. et al. | |
| 2017/0042593 A1 | 2/2017 | Newman et al. | |

OTHER PUBLICATIONS

International Patent Application No. PCT/US2015/059290; Int'l Preliminary Report on Patentability; dated May 18, 2017; 9 pages.

* cited by examiner

FLEXIBLE ADJUSTABLE RADIOPAQUE TRIAL, PLATE AND METHOD OF USE

CROSS-REFERENCE TO RELATED APPLICATIONS

The instant application is a continuation-in-part of U.S. patent application Ser. No. 15/588,375 filed May 5, 2017, which is a continuation of International Patent Application PCT/US2015/059290 filed Nov. 5, 2015, which claims the benefit of U.S. provisional patent application 62/075,717 filed Nov. 5, 2014. This application also is a continuation-in-part of International Patent Application PCT/US2017/058741, filed on Oct. 27, 2017, which claims the benefit of US provisional patent application 62/413,896 filed Oct. 27, 2016.

BACKGROUND

1. Field

This disclosure relates to a kit of disposable devices for assessment of positioning of implants, fixing devices such as screws and bone plate systems or connection devices.

2. General Background

Treating bone injuries may require the surgeon to remove diseased or damaged bone such as disc and utilize spacer or inserts in combination with plates, screws, cages and the like to affix adjacent vertebra together. For extremity repair of a bone such as the distal radius a plate is affixed to maintain the surgeon set or optimal set position during the bone healing period.

DISCLOSURE

Briefly stated, kits providing swappable disposable radiopaque spinal disc spacers or inserts of various sizes and an instrument to insert and remove, "swap", the spacers are disclosed. The inserts may be partially radiolucent and partially radiopaque to facilitate visualization under X-rays/fluoroscope. The trial plate may be partially radiolucent and partially radiopaque to facilitate visualization under X-rays/fluoroscope. At least two inserts of varying sizes are supplied with a kit. In some instance the trial plates are flexible.

Flexible plastic, resin or polymer material forming a trial plate for use in surgery of bones including spine and extremities. The trial plate having at least one radiopaque region and which may have one radiolucent region. In some instances a main body includes one or more arms formed of subparts. Between the main body and subparts and between the subparts are frangible regions such a ribs or unbroken edges surrounding windows configured as predetermined break points to disassociate portions of an arm from the whole Aspects of implementations include kits containing one or more of a flexible plastic, resin or polymer trial plates for use is surgery of bones including spine and extremities. The trial plate having at least one radio opaque region and guides for positioning. In a kit trial plates of varying sizes may be provided to customize the trial.

Aspects of implementations of devices and methods of flexible plastic, resin or polymer trial plates for use is surgery of bones include a flexible trial plate having a main body configured with at least one arm extending from the main body forming an elongated trial plate with adjustable arm(s) each extended arm provides at least one subarm. Subarms are partially separated from one another via one or more slots interposed between subarms; and, removal of subarms from an extended arm reduces the length of the trial plate. In some instances the slots are curved. The subarm(s) separated by slots are attached to each other and the main body through one or more frangible regions such as ribs or an unbroken side edge. In some instances an extended arm is reduced in size by disassociating other subarms via breaking or cutting a frangible region between subarms. At least a portion of the trial plate may be radiopaque. In some instances the curved slots approximates or defines the outline of an implant. In some instances a marker cue and/or a tool interface may be added.

Aspects of implementations of devices and methods of flexible plastic, resin or polymer trial plates for use is surgery of bones include a flexible trial plate having a main body configured with two arms extending from the main body forming an elongated trial plate with adjustable arms; each extended arm with at least one subarm. Subarms arm partially separated from one another via one or more slots and guides interposed between subarms; and, removal of subarms from at least one end of the extended arms reduces the length of the trial plate. In some instances at least one of the guides and the slots are curved. The subarms separated by slots are attached to each other and the main body through one or more frangible regions. In some instances an extended arm is reduced in size by disassociating other subarms via breaking or cutting a frangible region between subarms.

Aspects of implementations of devices and methods of flexible plastic, resin or polymer trial plates for use is surgery of bones include a flexible trial plate having a main body configured with arms extending from the main body forming an elongated trial plate with adjustable arms; each extended arm with at least one subarms. Subarms arm partially separated from one another via one or more slots or windows interposed between subarm and main body or between subarms; and, removal of subarm(s) reduce the length of the trial plate. In some instances the slots and/or windows are curved. In some instances the slots or windows are a complex shape formed of curved and straight regions. The subarms separated by slots are attached to each other and the main body through one or more ribs or unbroken edge regions. In some instances an extended arm is reduced in size by disassociating other subarms via breaking or cutting a frangible region between subarms. Break zones may be demarcated on unbroken edges to identify and/or facilitate breakage at specific points.

Aspects of implementations of methods of flexible plastic, resin or polymer trial plates for use in surgery to dynamically adjust an implant template include comparing a trial plate with a selected implant; and, if the trial plate is longer then the implant breaking at least one frangible region to remove a to reduce the length of the flexible trial plate. In some instances at least one of guides and shaped slots define the outline, perimeter or silhouette of the implant are provided between subarms wherein only frangible regions connect said subarms.

In some instances at least a portion of a trial plate is radiopaque and a portion is radiolucent. In some instances one of the trial plates and one of the inserts is more radiopaque than the other.

DRAWINGS

The above-mentioned features of the present disclosure will become more apparent with reference to the following description taken in conjunction with the accompanying drawings wherein like reference numerals denote like elements and in which:

FIGS. 10A and 10B show aspects of adjustable flexible trial plate As shall be appreciated by those having ordinary skill in the art, the figures are not to scale, and modifications to scale within a figure or across the figures are considered within the present disclosure.

FURTHER DESCRIPTION

Being disposable and single use the kit parts described herein avoid exposure of patients to radiopaque materials used herewith for all but a brief exposure. Further, the coating on coated embodiments may be extremely thin, to again limit the amount of such materials used or exposed to humans, due to the disposable nature of the kit parts.

Figure 1A:
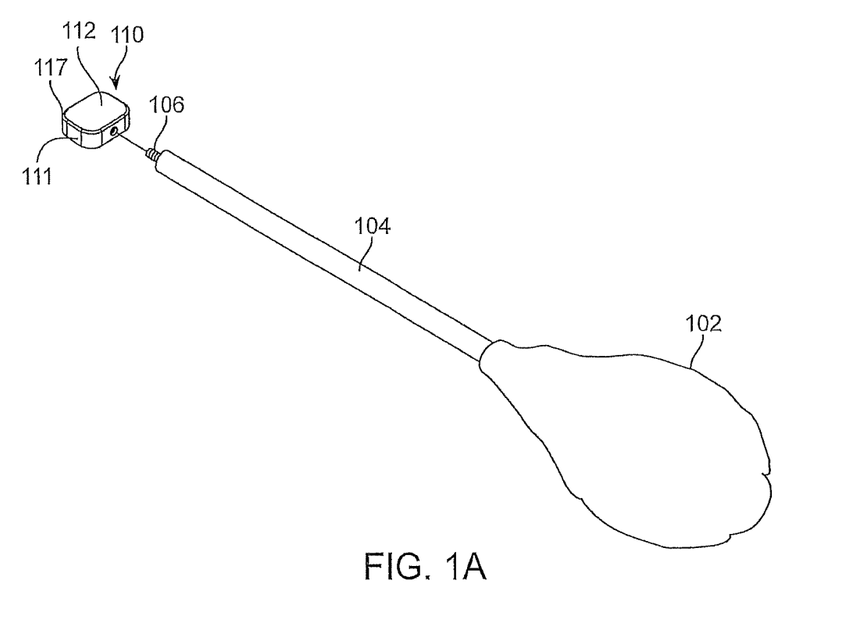
FIGS. 1A-1C are disc insert and tool.
Figure 1B:
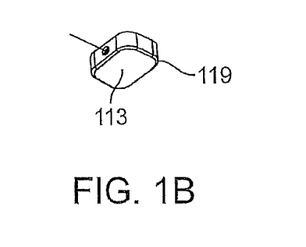
Figure 1C:
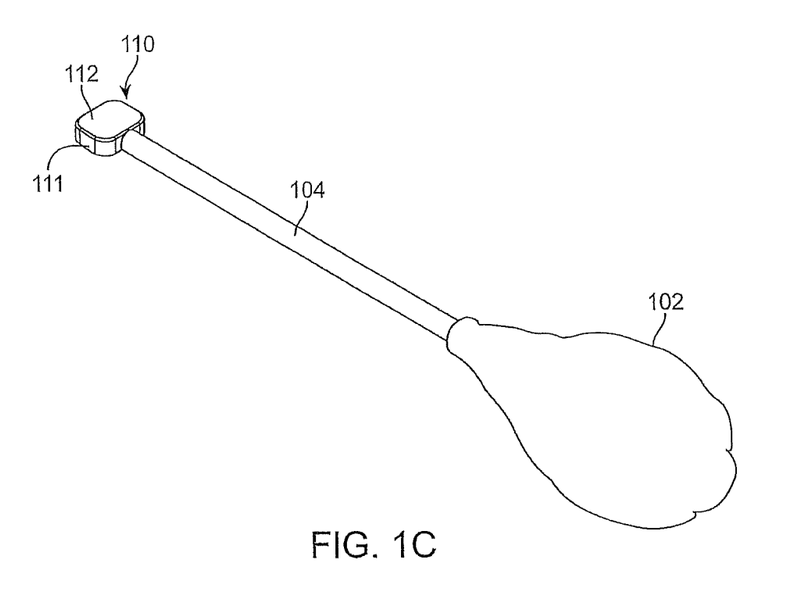

FIGS. 1A-1C show a tool 100 having a handle 102 for grasping and a shaft 104 affixed to the handle at one end and a free end 105 having a threaded connection 106. An insert 110 is disclosed of a size to approximate an intervertebral space. A kit may contain a plurality of inserts of varying sizes to give a surgeon choice in selecting the insert which best approximates an intervertebral space. The insert 110 is roughly a rounded square having an annular wall 111 surrounding a top surface 112 and a bottom surface 113. A threaded catch 115 is formed in the insert to mate with the threaded connection 106. The interface between the disc insert, top surface, and annular wall 111 forms a first perimeter 117 and the interface between the disc insert bottom surface and the annular wall 111 forms a second perimeter 119.

FIGS. 1A-6C show aspects of exemplary implementations of devices, methods and system which may include a kit with inserts 110 of various sizes. The inserts can be formed of plastic having radiopaque material therein. The insert may be coated with a radiopaque material or marker on one or more of a top surface 112, a bottom surface 113, an annular wall 111 and a perimeter 117/119. In some instances the insert may have radiolucent regions 120 or portions and radiopaque portions or regions 122.

Figure 2:
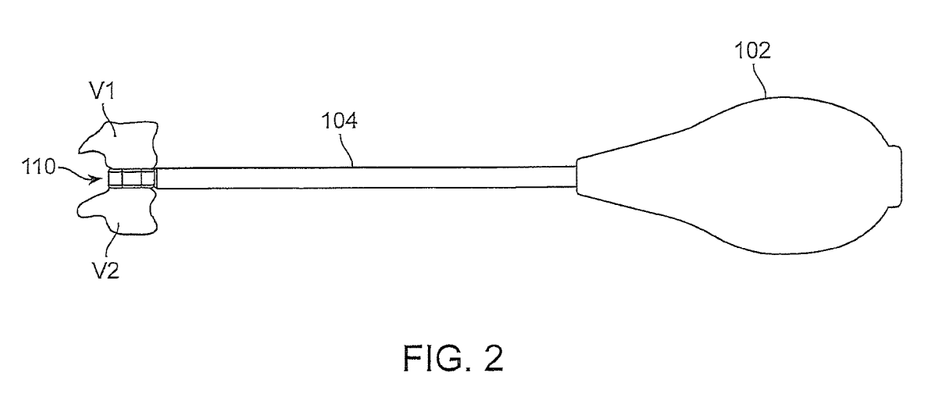
FIG. 2 shows a tool inserting a disc insert.
Figure 3:
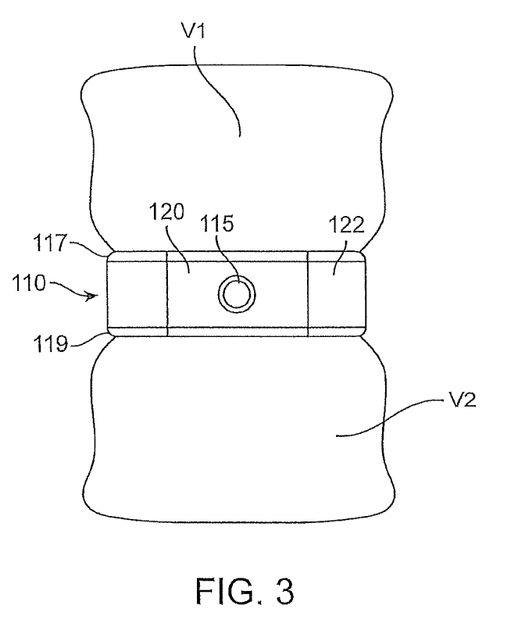
FIG. 3 shows a disc insert between vertebra.
Figure 4:
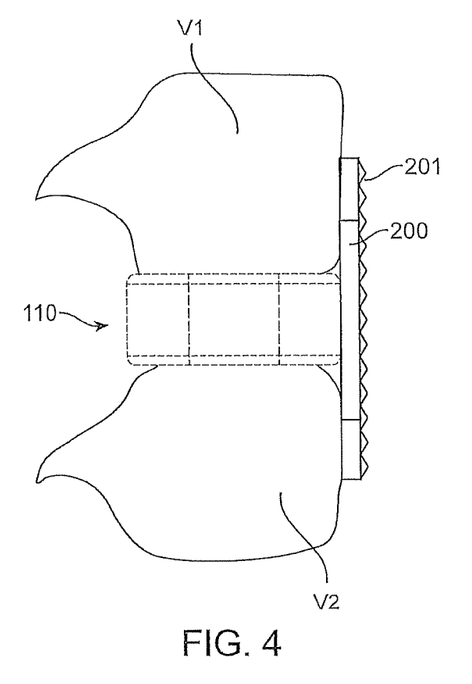
FIG. 4 shows a trial plate and disc insert.

When the tool 100 is connected to the insert 110, the insert is then inserted between a top vertebra "V1" and a bottom vertebra "V2".

A system and method of use includes a kit with various size and thickness inserts 110 each connectable to the tool. The surgeon assesses the physical space for an insert and tries various inserts to ascertain the right size for an implantable device. After assessing the size and height of the insert, which can include visualization of the insert between an upper vertebra and a lower vertebra via at least one radiopaque region 122, radiopaque coating or marker. After the size and shape for the final spinal disc spacer device (not shown) is assessed the insert is removed and replaced with a disc insert (not shown).

The insert 110 may have perimeters 117/119 and either perimeter, or a portion thereof, may be formed of or coated with a radiopaque material.

A trial plate 200 also disclosed. A trial plate mimics the size and shape of a plate, cage or other device used in spinal fusion procedures. Part of the kit may include different sized trial plates. The trial plate may be coated 201 with a radiopaque material.

Figures 5A, 5B:
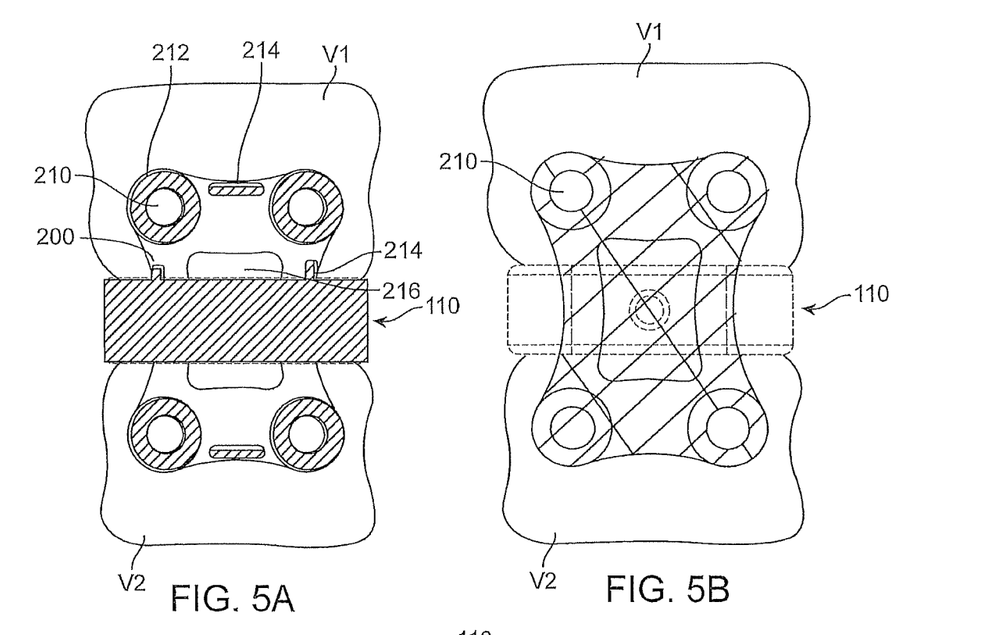
FIGS. 5A-5C show aspects of radiopaque or marked trial plates and an insert.

FIGS. 5A-6C show aspects of trial plate and insert combinations with varying radiopaque portions. Trial plates provide positioning guides 210 for the placement of drills, drill guides or fasteners (such as screws) for affixing a stabilizing device to vertebra during spinal fusion procedures. However, vertebra size and shape vary and a kit having multiple plates and/or inserts to choose from allows a surgeon to customize the fit to the patient. Having flexibility in the plate material further aids the surgeon in fit. In some instances radiopaque guide regions 212 surround positioning guides 210. In some instances radiopaque edge markers 214 are formed at the edges of the trial plate. In some instances radiolucent regions 216 are also provided on the trial plate. In FIG. 5A the insert 110 is radiopaque and visible through the radiolucent portion 216 of the trial plate 200.

Figure 5C:
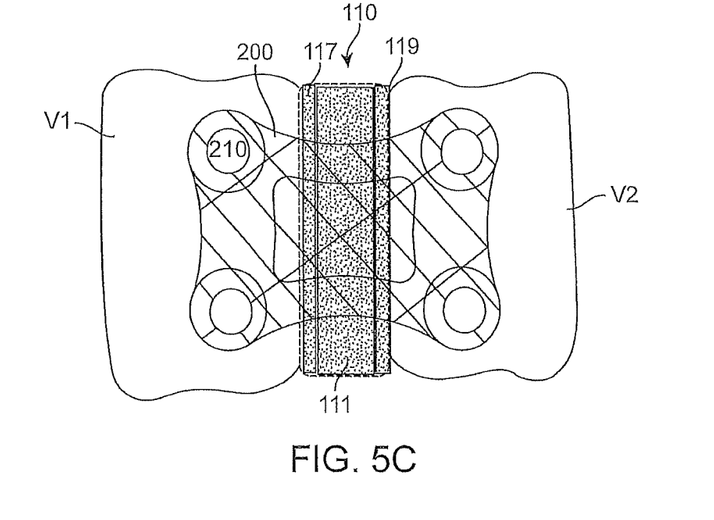

In FIG. 5B the trial plate is radiopaque except for the positioning guides 210. In FIG. 5C the trial plate 200 is radiopaque, but less radiopaque then the insert 110 or portions. thereof.

Figure 6A:
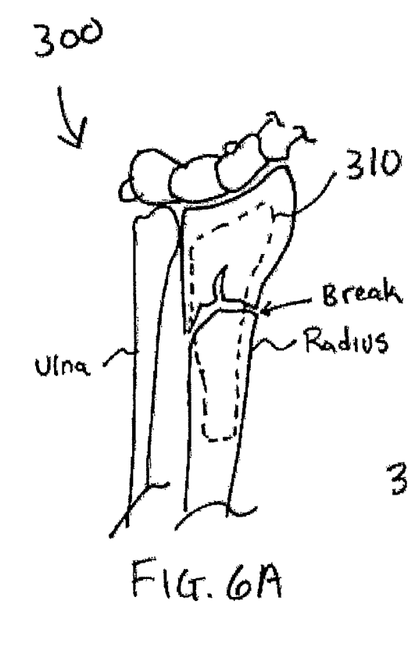
FIGS. 6A-6C show diagrams of the distal radius of a hand and flexible radiopaque trial plate.
Figure 6B:
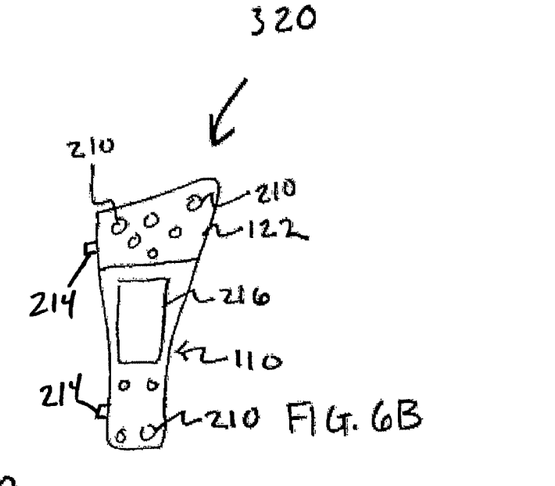
Figure 6C:
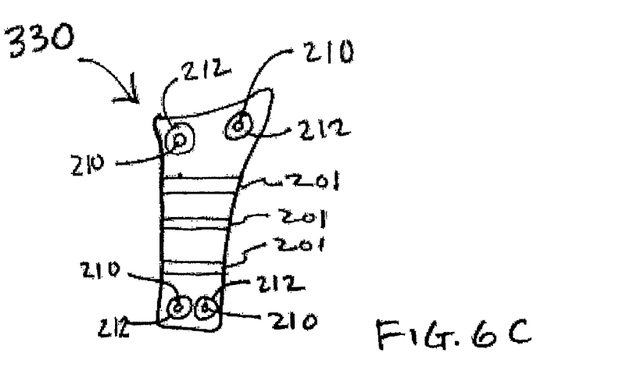

FIGS. 6A-6C illustrate a partial diagram of an arm/hand extremity and aspects of flexible radiopaque trial plates. FIG. 6A is a system overview of a flexible radiopaque trial plate and extremity 300. The Ulna and Radius are shown in conjunction with a flexible at least partially radiopaque trial plate 310. FIGS. 6B and 6C illustrate additional flexible at least partially radiopaque trial plates 320 and additional device 330 showing the placement of positioning guides, radiopaque and radiotranslucent material and/or coating on flexible trial plates and associated methods of use as described in references to FIGS. 4-5C.

By selection of concentrations of the radiopaque materials the insert or trial plate may be made distinguishable from the other. In some implementations, suitable materials for the insert or trial plate may include thermocomp (compound EX06430H from material manufacturer: Sabic Innovative Plastics, 1 Plastics Avenue Pittsfield, Mass. 01201), which may include barium sulfate and ULTEM™ polyetherimide resin; other suitable materials can include tantalum, gold, platinum, iridium, palladium, and rhodium and are well recognized for their biocompatibility. Radiopaque coatings can be applied to plastics using a high-vacuum deposition process that results in dense thin-film coatings (typically less than 10 μm) that adhere to the surface of the device.

One or more of Barium Sulfate ($BaSO_4$), Bismuth Subcarbonate ($Bi_2O_2(CO_3)$), Bismuth Oxychloride (BiOCl), Bismuth Trioxide ($Bi_2O_3$), Barium or any salt thereof: e.g., barium aluminate, barium carbonate, barium hydroxide, barium oxide, barium fluoride, barium sulfide, barium titanate and Tungsten (W) may be used to provide radiopacity to one or more inserts or trial plates in some implementations. Radiopaque materials may be combined with and mixed into materials used for injection molding and thereby distributed throughout at least a portion of a device so manufactured.

Additional radiopaque materials include iodine or salt thereof; organic iodine molecules used for contrast include iohexol, iodixanol, ioversol, diatrizoic acid [(or its anionic form, diatrizoate), also known as amidotrizoic acid, or 3,5-diacetamido-2,4,6-triiodobenzoic], Iothalamate (used as the meglumine or sodium salt, or a combination), Ioxaglate (Ioxaglic acid (trade name Hexabrix)). They also include lead and lead salts and they include Bismuth compounds, such as bismuth trioxide, bisthmuth subcarbonate, bismuth oxychloride.

Additional radiopaque materials include alloys of transition metals, especially Cr and Co, but also including Ag, Au, Cd, Hf, In, Ir, La, Mo, Nb, Os, Pd, Pt, Re, Rh, Ru, Pd, Sb, Sn, Ta, Te, V, W, and Zr.

Alloys comprising Co, Cr, Mo, Ni may be used as radiopaque coatings or additives. In some instances the plastic, resin or polymer base material contains or is coated with contains one or more of about 10% to 14% Cr; about 7% to 10% Ni; about 0.5% to 6% Mo; up to about 9% Co; about 0.5% to 4% Cu; and may include trace amounts of Al and Ti.

In some instances the flexible plastic, resin or polymer base material contains or is coated with contains one or more of chromium 12-20 wt %; Molybdenum 4 max. Tungsten 6 max. Cobalt 5-12 Iron 14 max.

In some instances the flexible plastic, resin or polymer base material contains or is coated with contains stainless steel, nitinol, tantalum, MP35N alloy, platinum, titanium In some instances the flexible plastic, resin or polymer base material contains or is coated with contains chromium; vanadium; molybdenum; cobalt; titanium; aluminum; zirconium; silicon; and nickel;

In some instances the flexible plastic, resin or polymer base material contains or is coated with contains nickel-cobalt-chromium alloy.

In some instances the flexible plastic, resin or polymer base material contains or is coated with contains nickel-cobalt-chromium-molybdenum alloy.

In some instances the flexible plastic, resin or polymer base material contains or is coated with contains chromium, and further containing molybdenum, nickel, cobalt, and tungsten, and minor amounts of at least one of aluminum, niobium, titanium and vanadium.

In some instances the flexible plastic, resin or polymer base material contains or is coated with contains nickel-titanium alloy including a ternary element selected from the group consisting of iridium, platinum, gold, rhenium, tungsten, palladium, rhodium, tantalum, silver, ruthenium and halfnium.

In some instances the flexible plastic, resin or polymer base material contains or is coated with contains nitinol, titanium, titanium-vanadium-aluminum alloy, cobalt-chromium alloy, cobalt-chromium-molybdenum alloy, cobalt-nickel-chromium-molybdenum alloy, biocompatible stainless steel, tantalum, niobium, hafnium, tungsten.

In some instances the flexible plastic, resin or polymer base material contains or is coated with contains stainless steel, Nitinol, cobalt-chromium-nickel-molybdenum-iron alloy, or cobalt-chrome alloy or chonichrome.

In some instances the flexible plastic, resin or polymer base material contains or is coated with a cobalt alloy comprising from 26 to 30 weight percent chromium, from 5 to 7 weight percent molybdenum, up to 1.0 nickel, up to 0.75 iron, up to 1.0 manganese, and greater than 50 weight percent cobalt.

In some instances the flexible plastic, resin or polymer base material contains or is coated with a radiopaque cladding layer selected from the group consisting of platinum, gold, tantalum, tungsten, a platinum-iridium alloy, and palladium.

In some instances the flexible plastic, resin or polymer base material contains or is coated with an alloy comprising, by weight: a) at least about 23% nickel; b) greater than 8% to about 17% molybdenum; c) greater than about 30% of a combination of chromium and molybdenum; d) from zero to about 5% cobalt; and e) greater than zero to about 50% iron.

In some instances the flexible plastic, resin or polymer base material contains or is coated with an alloy comprising iron, chromium, and a first element selected from a group consisting of platinum, ruthenium, palladium, iridium, rhodium, gold, and osmium, the alloy having less than about 0.03% by weight of nickel and having a radiopacity greater than the radiopacity of UNS S31673.

In some instances the flexible plastic, resin or polymer base material contains or is coated with at least 40% by weight of iron, from about 5% by weight to about 20% by weight of chromium, and greater than about 5% by weight of a first element having a density greater than 9.9 g/cc, the alloy having less than or equal to 1% by weight of nickel and having a radiopacity greater than the radiopacity of UNS S31673.

In some instances the flexible plastic, resin or polymer base material contains or is coated with a non-magnetic alloy comprising at least 40% by weight of iron, between about 5% and about 30% by weight of chromium, less than about 3% by weight of molybdenum, less than about 55% by weight of cobalt, less than about 20% by weight of manganese, less than about 6% by weight of copper, less than about 0.03% by weight of nickel, less than about 1.0% by weight of nitrogen, and between about 0.5% and about 40% by weight of a first element selected from a group consisting of platinum, ruthenium, palladium, iridium, rhodium, gold, and osmium, the alloy being substantially austenitic.

In some instances the flexible plastic, resin or polymer base material contains or is coated with a nonmagnetic nickel-cobalt-chromium-molybdenum [MP35N] alloy, platinum, titanium, a suitable biocompatible alloy, a suitable biocompatible material, and a combination thereof.

In some instances the flexible plastic, resin or polymer base material contains or is coated with alloy consists essentially of: from about 26 to about 28 weight percent chromium; from about 5 to 6 weight percent molybdenum; up to about 1 weight percent manganese; up to about 1 weight percent nickel, up to about 0.75 weight percent iron; up to about 0.07 weight percent carbon.

In some instances the flexible plastic, resin or polymer base material contains or is coated with a cobalt-chromium alloy comprising by weight percent: about 60 to about 85% cobalt; about 15 to about 30% chromium; about 4 to about 20% manganese; and about 1 to about 15% Al, In, GA, Sn, or Ge, or mixture thereof; optionally further comprising up to about 20% Fe, Ni, Pd, or Pt, or mixture thereof; up to about 10% gold; up to about 15% Ta, Nb, Mo, W, or V or mixture thereof; up to about 6% Ir, Ru, Re, Ti, Si or Cu or mixture thereof; and up to about 5% Zr, Hf, B, Y, or a rare earth metal or mixture thereof.

In some instances the flexible plastic, resin or polymer base material contains or is coated with a cobalt-chromium dental alloy comprising by weight percent: about 65 to about 80% cobalt; about 18 to about 25% chromium; about 4 to about 10% manganese; about 2 to about 10%, iron, nickel, palladium, or platinum, or mixture thereof; about 1 to about 7% Al, In, Ga, Sn, or Ge, or mixture thereof; about 1 to about 5% gold; and about 0.1 to about 3% Ir, Rum Re, Ti, Si, or Cu, or mixture thereof; optionally further comprising up to about 5% Ta, Nb, Mo, W, or V, or mixture thereof, and up to about 1% Zr, Hf, B, Y, or a rare earth metal, or mixture thereof.

In some instances the flexible plastic, resin or polymer base material contains or is coated with a metal selected from the group consisting of platinum, gold, tantalum, tungsten, platinum-iridium and palladium.

In some instances the flexible plastic, resin or polymer base material contains or is coated with stainless steel 316L, nitinol, a cobalt-chromium alloy, and other materials of similar radiopacity, plus an metal selected from the group comprising gold, gold alloys, tantalum, tantalum alloys, platinum, platinum alloys and other materials of similar radiopacity including 316 stainless steel, MP35N alloy, and 35NLT alloys; L-605 chromium-cobalt-tungsten-nickel alloys (nominally 19-21 wt % Cr, 14-16 wt % W, 9-11% Ni)

To make the insert or trial plate distinguishable from the other the perimeter 117/119 may be radiopaque and the edge or annular wall 111 not, or vice versa. Or the perimeters may be more radiopaque than the trial plate 200, 310, 320, 330 or portions thereof.

Additional suitable materials for an insert or flexible trial plate base material (which is then coated with or has incorporated into a radiopaque material as previously mentioned) may include polypropylene (i.e., polyolefins, including polyethylene, polypropylene, polybutylene, etc), polyacrylate or methacrylates, polyalkyl(meth)acrylates), polypropylene sulfides, polybutylene terephthalates (including polyalkylene terephthalates or naphthalates). Pegylated copolymers, including pegylated styrenic block copolymer matrices; Polyurethanes, poly(N-vinylpyrrolidones), polycarbonates, polyphenylene oxides, polysiloxanes, phenoxy and epoxy resins. Additional compounds include synthetic polymers include, but are not limited to, aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polysiloxanes, and combinations thereof. More specifically, biosynthetic polymers based on sequences found in poly(amino acid), poly(propylene fumarate), polyethylene, polyethylene terephthalate, poly(tetrafluoroethylene), polycarbonate, polypropylene and poly(vinyl alcohol), and combinations thereof. Examples of biodegradable polymers include aliphatic polyesters, poly(amino acids), polyalkylene oxalates, polyamides, polyamido esters, poly(anhydrides), poly(beta-amino esters), polycarbonates, polyethers, polyorthoesters, polyphosphazenes, and combinations. More specific examples of biodegradable polymers include, but are not limited to, collagen (e.g., Collagen I or IV), fibrin, hyaluronic acid, polylactic acid (PLA), polyglycolic acid (PGA), polycaprolactone (PCL), poly(Lactide-co-Glycolide) (PLGA), polydioxanone (PDO), trimethylene carbonate (TMC), polyethyleneglycol (PEG), Collagen, PEG-DMA, or copolymers or mixtures thereof. Examples of non-biodegradable polymers include, but are not limited to, carbon, nylon, silicon, silk, polyurethanes, polycarbonates, polyacrylonitriles, polyanilines, polyvinyl carbazoles, polyvinyl chlorides, polyvinyl fluorides, polyvinyl imidazoles, polyvinyl alcohols, polystyrenes and poly(vinyl phenols), aliphatic polyesters, polyacrylates, polymethacrylates, acylsutostituted cellulose acetates, nonbiodegradable polyurethanes, polystyrenes, chlorosulphonated polyolefins, polyethylene oxides, polytetrafluoroethylenes, polydialkylsiloxanes, and shape-memory materials such as poly(styrene-block-butadiene), copolymers or mixtures thereof.

In addition to the above materials thermoset or thermoplastic polymers or polymer resins, elastomers, or mixtures thereof may be used for the flexible trial plate base material which include those wherein the polymer or polymer resin contains an aromatic or heteroaromatic moiety, for example, phenyl, biphenyl, pyridinyl, bipyridinyl, naphthyl, pyrimidinyl, including derivative amides or esters of terephthalic acid or naphthalic acid. Examples include those where the polymer or polymer resin comprises polyester, polyamide, polyethylene, polypropylene, polyethylenenaphthalate (PEN), polyethylene terephthalate (PET), polybutylene terephthalate (PBT), polyether etherketone (PEEK), polyamide, polyaryletherketone (PAEK), polyethersulfone (PES), polyethylenenimine (PEI), poly (p-phenylene sulfide) (PPS), polyvinyl chloride (PVC), fluorinated or perfluorinated polymer (such as a polytetrafluoroethylene (PTFE or TEFLON®), polyvinylidene difluoride (PVDF), a polyvinyl fluoride (PVF or TEDLAR®))

Figure 7:
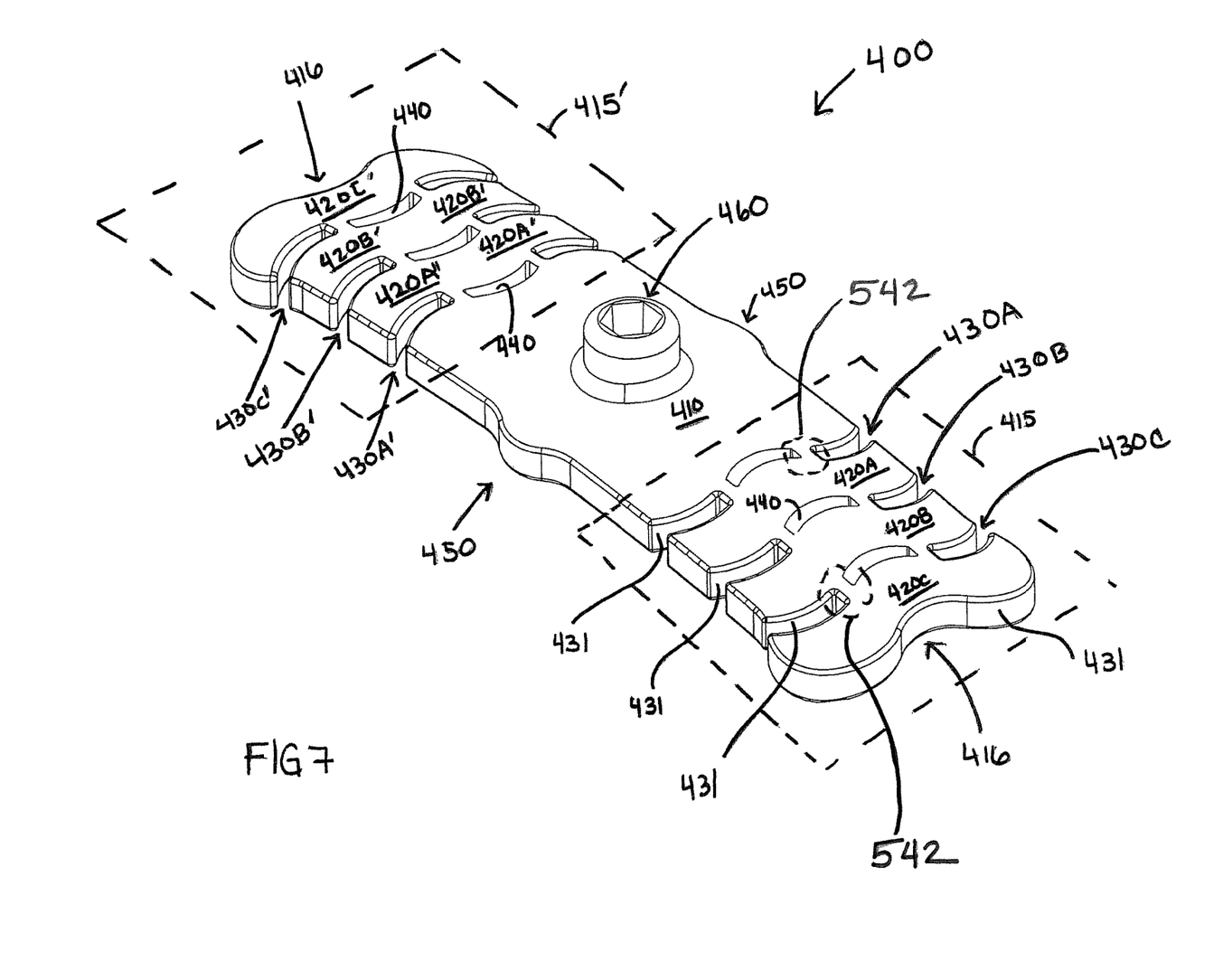
FIGS. 7 and 8 show aspects of an adjustable flexible trial plate.
Figure 8:
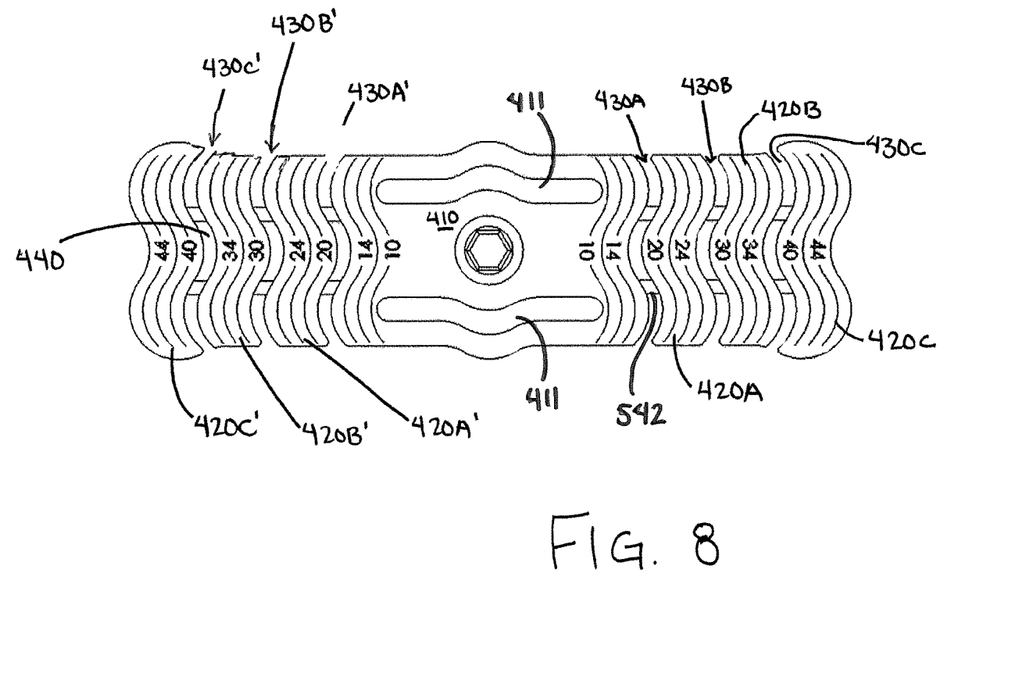

Shown in FIGS. 7 and 8 are aspects of a trial plate 400 that is a dynamic adjustable template or trial which may be one of radiopaque, have radiopaque regions or gradients, non-radiopaque. A main body 410 is shown with two extended arms 415 and 415'. In some instances at least one window gap 411 is formed by an annular wall is provided for visualization of structure below the device. Those of ordinary skill in the art will understand that a single armed variant wherein one of arms 415 and 415' is removed is optionally a variant for some uses and is also within the scope of the disclosure. Each arm having an end 416 and each arm is configured into at least one subarms 420A-420C and 420A'-420C' which are further separated from the main body and each other by adjustment openings or slots 430A-430C and 430A'-420C'. The slots may be further configured to form shaped gaps. Additional one or more windows, also referred to as separation guides or guides 440 formed by an annular wall 412 through the arm may be placed between subarms. As illustrated in FIGS. 9A-10B the slotted regions may be curved, straight or a combination of curves and straight sections.

Figure 9:
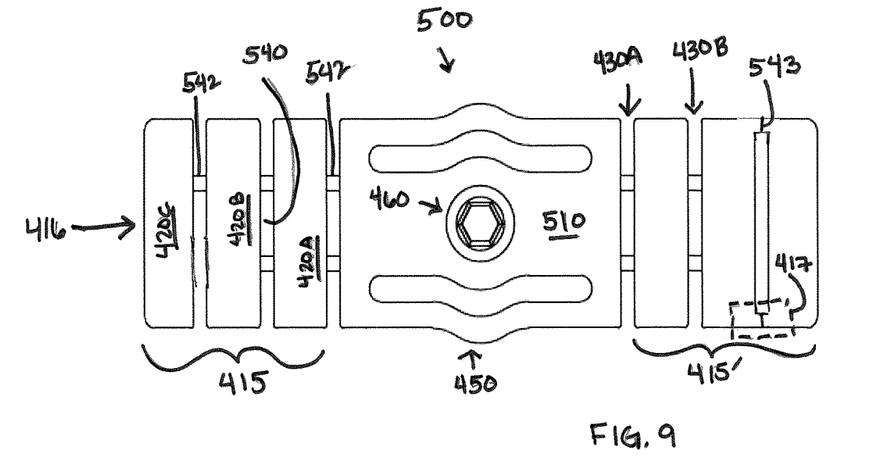
FIG. 9 shows aspects of adjustable flexible trial plate.

FIG. 9 shows aspects of an implementation 500 with a body 510, with two extended arms 415 and 415' and subarms 420A-420C with straight slots 430A-430C and a window 540 through the subarm separating said subarm from the adjacent subarm via one or more connecting rib 542. The location of the connecting ribs as shown in FIG. 9 may be anywhere along the slot thereby forming a window. The connecting ribs are generally perpendicular to the subarms. The subarms may also be attached to an adjacent subarm or the main body via an unbroken edge 417. A break zone 543 may be added to mark and/or provide a frangible region to disassociate at. The connecting ribs may be a lesser thickness that the arms, a greater thickness or the same thickness. The connecting ribs may be configured to be frangible through adjustment of said thickness. Forming slots or gaps or windows adjacent to ribs or frangible regions provide for visual inspection of areas under the trial plate between subarms.

Break zones 543 which include but are not limited to divots, indentations, grooves, thin areas and weak regions may be formed in the arm configured to facilitate breakage at a designated area.

Figure 10A:
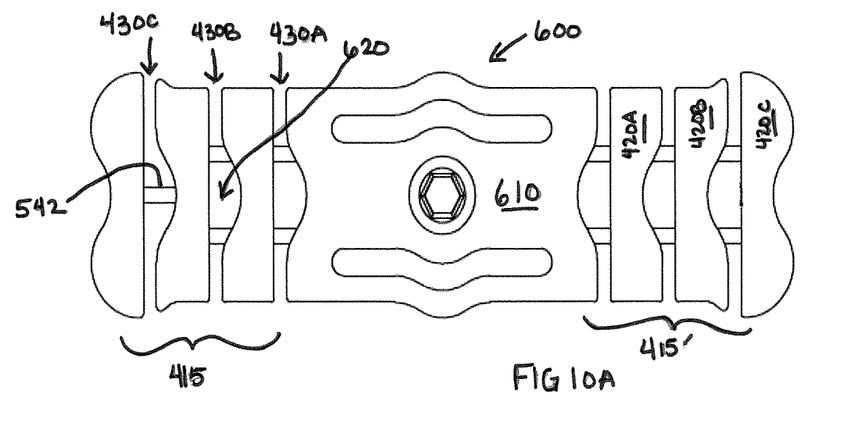
Figure 10B:
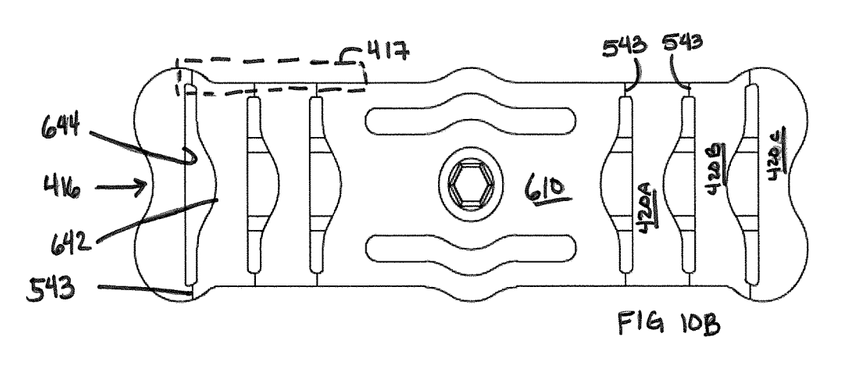

FIGS. 10A and 10B shows aspects of an implementation 600 with a body 510, with two extended arms 415 and 415' and subarms 420A-420C. Non-parallel slots 430A-430C and a non-rectangular window 620 comprising curved portions 642 and straight portions 644 window through which a subarm is separated from the adjacent subarm via one or more connecting rib 542 or an unbroken edge which may have a break zone 543. The connecting ribs and/or break zone form a gap between the subarms.

The slots and windows cooperate to form frangible regions configured to provide a weak area at which subarms may be disassociated from the arm, body and/or the trial plate. Rib or ribs 542 may be formed between subarms or the body and arm are interposed at edges or through the slot to connect adjacent arm members. The ribs are configured to be frangible or small enough in size to be subject to manual cutting.

Disassociation of subarms is used to dynamically customize the length of said trial plate. The slots (as shown in FIGS. 7-8D) may be open, closed, straight, curved, or a complex shape of curves and straight regions. The shape the guide or guides outline is configured to approximate a predetermined shape such as the shape of an implant the trial plate is used with whereby the implant (not shown) can be visualized to prepare a site for surgery, implantation and the like. Between two ribs the area of slot may be referred to as a window. The slots are an adjustment means as such they may be straight or form a complex non-linear path providing at least one of a visualization of an implant and a weakened area that can be broken to reveal the side edge 431 of the remaining portion of a subarm and thereby approximating the shape and size of an implant. The slots define an absence of material in the trail plate. Subarms are connect to adjacent subarms and the main body (410) via frangible regions. In some instances additional guides 440 are also provided near slots. Although one additional guide 440 per subarm is shown, those of ordinary skill in the art will understand that a plurality of additional guides may be added without departing from the scope of the invention (See FIG. 10B). The separation guide may be configured to provide a further silhouette or path to shape an edge 431 which will be revealed after breaking off or otherwise disassociating sub-arm 420C from the device. The slots define a silhouette/outline or shape of the side edge. Separation guides adjacent to slots cooperate with the slots to define the silhouette or edge of a subarm.

On either side of the center of the trial plate 400 bumps (in one exemplar) are shown forming a visual and/or tactile marker 450. Although shown as extended lateral edges from the trial plate, they may also be indentations, raised sections or indentations. The purpose of the markers are to provide a cue about where an implant would be positioned. The edges or subarms or body of the trial plate may be radiopaque to facilitate viewing of same. Finally, a driver interface 460 is provide on the trial plate to form a connection with a tool used to one of hold, move, insert and remove the trial plate.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. An adjustable implant template comprising:
a flexible trial plate (400) having a main body (410) and configured with two arms (415 and 415') extending from the main body;
each extended arm further comprising;
at least one subarm extending from each arm (420);
one or more ribs (542) formed between subarms configured to form a window (440) and an open viewing slot (430) and to connect subarms;
wherein each viewing slot and window is configured to provide visualization of an implant;
one or more slots (430) interposed between subarms and partially separating subarms; and,
wherein removal of a subarm from at least one end of the an arm reduces the length of the trial plate.

2. The template of claim 1 wherein the slots are straight.

3. The template of claim 1 wherein the slots are curved.

4. The template of claim 1 wherein the slots have curved and straight portions.

5. The template of claim 1 further comprising at least one of a rib (542) and unbroken edge (417) formed between subarms configured to connect subarms.

6. The template of claim 1 wherein the rib or unbroken edge is frangible.

7. The template of claim 6 wherein an extended arm (415/415') is reduced in by removal of a subarm by disassociating said subarm via breaking or cutting a frangible rib or unbroken edge.

8. The template of claim 5 wherein a window is formed between two ribs.

9. The template of claim 1 further comprising a portion of the trial plate is at least one of radiopaque and radiolucent.

10. The template of claim 2 wherein slot shape approximates the outline of an implant.

11. The template of claim 1 further comprising a marker (450) cue.

12. The template of claim 1 further comprising a tool interface (460).

13. An adjustable implant template comprising:
a flexible trial plate (400) having a main body (410) and configured with two arms (415 and 415') extending from the main body;
each extended arm further comprising;
at least one removable subarm (420) with one or more ribs (542) formed between subarms configured to form a window (440) and an open viewing slot (430) and to connect subarms;
wherein each slot and window is configured to provide visualization of an implant;
at least one unbroken edges configured to form a slot or gap between adjacent subarms;
a break zone (543) formed on at least a portion of the unbroken edge; and,
a guide edge (431) of the subarm is visible through the gap or slot.

14. The template of claim 13 wherein the slots approximates the outline of an implant.

15. A method of dynamically adjusting an implant template, the method comprising:
placing a trial plate (400) with one or more ribs (542) formed between subarms configured to form a window (440) and an open viewing slot (430) and to connect subarms over a selected implant; and,
disassociating at least one subarms from an extended arms of said trial plate by breaking or cutting a an unbroken edge or rib connecting the at least one subarms to the trial plate; and,
whereby the length of the flexible trial plate (400) is reduced; and,
wherein each slot and window is configured to provide visualization of an implant under the trial plate.

16. The method of claim 15, the method further comprising providing at least one of slots and windows between subarms configured to generally define the outline of the selected implant.

17. The method of claim 15, the method further comprising providing at least one of windows and slots between subarms to reduce the mass of ribs.

18. The method of claim 15, wherein a portion of the trial plate is one of radiopaque and radiolucent.

* * * * *